United States Patent [19]

Reussner et al.

[11] 4,277,464
[45] Jul. 7, 1981

[54] PREVENTING TOOTH DEMINERALIZATION USING ASPARTAME

[75] Inventors: George H. Reussner; Reinhardt Thiessen, Jr, both of Pearl River, N.Y.

[73] Assignee: General Foods Corporation, White Plains, N.Y.

[21] Appl. No.: 24,810

[22] Filed: Mar. 28, 1979

Related U.S. Application Data

[63] Continuation of Ser. No. 614,995, Sep. 19, 1975, abandoned.

[51] Int. Cl.³ .............. A61K 37/00; A61K 7/16; A23L 1/236; A23J 1/00
[52] U.S. Cl. .................. 424/177; 424/49; 424/54; 426/548; 426/656
[58] Field of Search .............. 424/177, 49, 54; 426/548, 656; 260/112.5 R

[56] References Cited

U.S. PATENT DOCUMENTS

| 3,475,403 | 10/1969 | Mazur et al. | 260/112.5 |
|---|---|---|---|
| 3,492,131 | 1/1970 | Schlatter | 426/548 |
| 3,642,491 | 2/1972 | Schlatter | 426/548 |
| 3,928,560 | 12/1975 | Neely et al. | 424/52 |
| 3,934,047 | 1/1976 | Schade | 426/548 |

*Primary Examiner*—Douglas W. Robinson
*Attorney, Agent, or Firm*—Joyce P. Hill; Mitchell E. Alter

[57] ABSTRACT

The addition of effective amounts of selected peptides, preferably dipeptides such as L-aspartyl-L-phenyl-alanine methyl ester (aspartame), to dental caries supporting food products reduces the tendency toward the occurrence of dental caries. Also, the addition of these peptides to low pH beverages reduces the tendency toward tooth enamel demineralization as well as dental caries.

7 Claims, No Drawings

PREVENTING TOOTH DEMINERALIZATION USING ASPARTAME

CROSS REFERENCE TO RELATED APPLICATION

This is a continuation of application Ser. No. 614,995, filed Sept 19, 1975, now abandoned.

BACKGROUND OF THE INVENTION

The present invention relates to dental health and food products, and specifically to the reduction of dental caries and tooth enamel demineralization caused by a wide variety of food products.

A number of food products have caused concern in recent years as being possibly related to decreased dental health in the persons consuming them. This concern has prompted a good deal of research to either prove or disprove the relationship, as well as research directed toward finding ways of eliminating the problems with respect to these products.

Principally cited as having possible connection with decreased dental health are foods high in acid and those high in sucrose content. Recent studies with rats, for example, have indicated that continued consumption of low pH beverages, whether natural or artificial, can result in a generalized demineralization of the teeth. In this regard, see for example: Wagg et al., *British Dental Journal*, vol. 119, No. 3, pages 118 through 123, Aug. 3, 1965; and McDonald Jr., et al, *J. Dent. Res.*, March-April 1973, pages 211-216. Some investigators have indicated that certain phosphates, such as calcium phosphates may inhibit this form of demineralization or may, in fact, effect remineralization of teeth demineralized in this manner. In this regard, see for example: Wagg et al, supra; Picket et al., *The Alabama Journal of Medical Sciences*, vol. 2, No. 3, July 1965; Silverstone et al, *Caries Research*, 5:323-342, 1971; and U.S. Pat. No. 3,375,168 to J. H. Curtin et al. Additives such as calcium phosphates have not, however, completely eliminated the problem.

While there is evidence on both sides of the question, it can be safely said that sucrose does, under many circumstances of use in food products, result in increased dental caries. Exemplary of teachings of this kind is Scherp, *Science*, Vol. 173, No. 4003, pages 1199-1205. With all the discussion and research in this area, there is still a need for an additive which can mitigate the problem of dental caries caused by food products which have been identified as troublesome.

SUMMARY OF THE INVENTION

It is an object of the present invention to provide additives for food products which are effective to reduce the causation of dental caries and tooth enamel demineralization by food products which would normally foster these problems.

This object, and others which will be apparent to those skilled in the art upon reading this disclosure, is accomplished by adding selected peptides, preferably dipeptides such as L-aspartyl-L-phenylalanine methyl ester (aspartame), to food compositions normally causative of dental caries or tooth enamel demineralization. The peptides are added alone or in combination in any amount effective to cause a decrease in dental caries and/or tooth enamel demineralization over that which would normally occur when the food product is consumed.

The use of the peptides generally, and aspartame in particular, which is well known as a sweetener (see for example U.S. Pat. No. 3,642,491 to J. M. Schlatter), to provide food products of improved dental health is believed new and should be effective over a wide range of concentrations in the food products. Specifically, preferred concentrations for aspartame, and the other sweet dipeptides, are those above and below the levels thought by those skilled in the art to provide desirable levels of sweetness. However, the invention envisages all novel levels of the dipeptides in food products where they are present, alone or in combination, in amounts effective to mitigate the causation of dental caries and/or tooth enamel demineralization over that which would normally occur. Where sucrose is the cariogenic agent, amounts of the peptides within the range of from about 0.1 to 10 parts of dipeptide for each 100 parts of sucrose are believed effective.

Within the conception of the present invention are all those acidic peptides which effect a rise in the pH of a dilutely acid (e.g. pH 2-5) aqueous solution. Specifically useful are aspartame, L-aspartyl-L-phenylalanine, L-aspartylglycine and L-aspartyl-L-alanine. Also contemplated are the other peptides, especially oligopeptides such as di-and tri-peptides, of the acidic amino acids, e.g. aspartic acid and glutamic acid, with non-basic amino acids such as alanine, cystine, tyrosine, phenylalanine, glycine, leucine, isoleucine, proline, methionine, valine, threonine, and tryptophane. Specifically suggested of this group are L-tyrosyl-L-glutamic acid, L-tyrosyl-L-aspartic acid, L-alanyl-L-glutamic acid and L-alanyl-L-aspartic acid.

The types of products in which these peptides can be employed for their advantageous effect on dental health are broad and their effectiveness according to this invention is not presently known to be limited by any factors present in food products. A representative listing of the various food products which can advantageously enjoy the benefits of the present invention is as follows:

Breads
Breakfast Cereals
Cakes
Candies
Carbonated Beverages
Chewing Gum
Chocolates
Coffee Lighteners
Cookies
Dry Beverage Mixes
Farinaceous Snack Items
Flavored Ices
Frostings
Fruit Concentrates
Fruits
Desserts
Ice Cream
Juices
Puddings
Sherbets
Syrups
Table Sugar
Whipped Toppings As indicated, this list is merely representative and is not exhaustive of the types of food products contemplated herein.

DESCRIPTION OF PREFERRED EMBODIMENT

While the scope of products which can be improved by the present invention is broad, the following disclosure will relate specifically to a low pH beverage mix. This product is dealt with as only exemplary and should not be taken as limiting of the invention.

In the low pH beverage products as with the other products encompassed by the present invention, the amount of peptide employed can be any amount which is effective to attain the objects of the invention. Preferably, however, where the peptide has a sweetening effect, such as aspartame, it is employed at a level insufficient by itself to provide a desirably sweet beverage or at a level greater than that necessary, when used alone or in combination with another sweetener, to provide the desirable sweetness in the beverage. While these variations in level of sweetness from conventional beverages may at first seem unusual to the consumer, it is believed that the improvement in dental health achieved over conventional beverages should outweigh any adverse reaction in this regard.

For the purposes of the present invention a low pH beverage is defined as one having an acid pH, e.g. below about 6 and preferably below about 5, and containing from about 0.015 to about 0.15 gram equivalents of an edible acid per quart of beverage.

Beverages of this type are well known and typically comprise an aqueous solution of a flavorant, a colorant, a sweetener, a food acidulent. Also, these beverages can contain buffers to control acidity, gums to provide texture and clouding compositions to provide a degree of opacity to the beverage. Beverages of this kind can also include various food and nutritional supplements such as vitamins and minerals. Vitamins A and C are typical of such additives.

Typical of the edible acids which can be employed are citric, malic, adipic and fumaric acids. These acids can be employed alone or in combination and can be supplemented or replaced by other conventional food acidulents.

A wide variety of flavorants are known for use in beverages of the kind considered here. Typical of these are natural and artificial flavorants such as cherry, strawberry, grape, orange, lemon, lime, root beer, cola, raspberry, grapefruit, fruit punch, and the like, which are employed in suitably effective amounts.

Apart from the aspartame which has a sweetening effect at known concentrations, but which is not employed according to the present invention primarily as a sweetener, sweetness can be obtained using any of the known, edible natural or synthetic sweeteners. Of the natural sweeteners, sucrose is the most common; however, other sugars such as fructose, dextrose, etc.; certain amino acids such as L-alanine and glycine; certain alcohols such as sorbitol, mannitol and xylitol; and certain vegetable extracts such as glycyrrhiza globra; and the like, can be employed. Exemplary of the synthetic sweeteners which can be employed are saccharin and saccharin salts, cyclamate and cyclamate salts, and certain dipeptides and their salts.

The aspartame or other peptide is employed to effect the objects of the present invention at levels of from about 0.25 to about 2.00 grams per quart of beverage or an amount of dry mix for preparing the same. Preferably it is employed at levels of from about 0.50 to about 0.75 grams per quart of beverage or mix therefor.

One preferred beverage contains a less than sweetening amount of aspartame along with sucrose in a sweetening amount, e.g. about 25 to about 100 grams of sucrose per quart of beverage or mix therefor, and from about 0.25 to about 0.50 grams of aspartame per quart of beverage, the beverage, thus, having a total amount of sweetener greater than would be normally desired. This beverage preferably contains from 0.015 to 0.08 gram equivalents of acid per quart of beverage. In this embodiment, the caloric value of the sucrose is present in the beverage, but the cariogenic propensities thereof are reduced, not only due to the reduced level of sucrose added, but also due to the protective effect of the aspartame. The excess sweetness can be reduced, if desired, by adding to the beverage a sweetness modulating material such as alum, naringin, or the like.

The ingredients are preferably dry blended to form the mix and can be agglomerated, as by steam agglomeration, if desired. The mix ingredients are preferably packaged by volumetric metering devices into conventional plastic coated foil packs to preserve freshness.

The following specific examples are presented for the purpose of further illustrating the present invention, and are not to be taken as limiting in any regard. Unless otherwise indicated, all parts and percentages are by weight.

EXAMPLE I

A relatively low acid instant beverage mix according to the present invention is prepared by dry mixing the following materials:

| Ingredients | Parts |
| --- | --- |
| Citric acid, anhydrous | 41.1 |
| Monocalcium Phosphate | 34.3 |
| Aspartame | 12.6 |
| Carrier for Aspartame (hydrolyzed cereal solids) | 8.4 |
| Flavorant | 1.8 |
| Vitamin C | 1.3 |
| Colorant | 0.5 |
| Vitamin A | 0.14 |

About 4.4 grams of this mix are added to a quart of water to provide a pleasing beverage having the advantages of the present invention.

EXAMPLE II

A beverage mix having a slightly higher acid content than that of Example I is prepared by dry mixing the following ingredients:

| Ingredients | Parts |
| --- | --- |
| Citric acid, anhydrous | 57.5 |
| Monocalcium Phosphate | 16.4 |
| Trisodium Citrate | 8.8 |
| Aspartame | 5.5 |
| Carrier for Aspartame (hydrolyzed cereal solids) | 1.8 |
| Flavorant | 6.0 |
| Cloud | 3.3 |
| Vitamin C | 0.6 |
| Vitamin A | 0.07 |

About 9 grams of this mix are added to a quart of water to provide a pleasing beverage having the advantages of the present invention.

EXAMPLE III

A further beverage mix, having a relatively high acid content, is prepared by dry mixing the following ingredients:

| Ingredients | Parts |
|---|---|
| Dextrin | 58.4 |
| Aspartame | 1.8 |
| Citric Acid | 19.0 |
| Cloud | 5.6 |
| Monocalcium Phosphate | 4.0 |
| Potassium Citrate | 2.8 |
| Tricalcium Phosphate | 2.4 |
| Vitamin C | 1.5 |
| Orange Flavorant | 2.6 |
| Vegetable Gum | 1.8 |
| Vitamin A | 0.1 |
| Color | 0.15 |

About 34 grams of this mix are added to a quart of water to provide a pleasing simulated orange juice having the advantages of the present invention.

EXAMPLE IV

A gelatin dessert mix is prepared by dry mixing the following ingredients:

| Ingredients | Parts |
|---|---|
| Gelatin | 55.6 |
| Adipic Acid | 23.3 |
| Fumaric Acid | 2.6 |
| Potassium Citrate | 9.4 |
| Strawberry Flavors fixed in vegetable gum | 1.0 |
| Strawberry Color fixed in vegetable gum | 0.3 |
| Aspartame | 7.9 |

About 13 grams of this mix are dissolved in one cup of boiling water by stirring. One cup of cold water is then added and mixed. The total solution is then chilled to set the gelatin, thereby providing a strawberry flavored gelatin dessert having the benefits of the present invention.

EXAMPLE V

A pudding and pie filling mix is prepared by mixing the following dry ingredients:

| Ingredients | Parts |
|---|---|
| Sucrose | 49 |
| Dextrose | 21 |
| Pregelatinized Starch | 15 |
| Cocoa | 13 |
| Disodium Orthophosphate | 2.3 |
| Tetrasodium Pyrophosphate | 1.5 |
| Mono and diglycerides | 0.3 |
| Non fat milk solids | 0.1 |
| Lecithin | 0.2 |
| Salt | 0.2 |
| Hydrogenated Vegetable Oil | 0.15 |
| Brown Color | 0.07 |
| Vanillin | 0.06 |
| L-Aspartyl-L-Phenylalanine | 1.0 |

Approximately 128 grams of this mix is thoroughly mixed with 2 cups of cold milk for about 2 minutes and allowed to set to form a chocolate pudding.

EXAMPLE VI

A similar composition to that prepared in Example V is prepared by employing 2.0 parts of the L-aspartyl-L-phenylalanine.

EXAMPLE VII

A sugar coated breakfast cereal is prepared by employing as a coating for a puffed rice cereal the following dry ingredients dissolved in water:

| Ingredients | Parts |
|---|---|
| Sucrose | 90 |
| Cocoa | 5 |
| Corn Syrup | 6 |
| Salt | 1.5 |
| Flavors | 0.6 |
| Vitamins & Minerals | 0.2 |
| L-aspartylglycine | 1.0 |

The solution is sprayed onto the puffed rice in a gas fired dryer of conventional construction to coat and dry the cereal product. The final product contains about 50% of the dry coating mixture.

EXAMPLE VIII

A cereal product similar to that of Example VII is prepared, but this time 3 parts of monocalcium phosphate are added to the coating solution and the amount of L-aspartyl-glycine is increased to 2.0 parts.

EXAMPLE IX

A further dry beverage mix is prepared having the following dry ingredients:

| Ingredients | Parts |
|---|---|
| Sucrose | 89.28 |
| Citric Acid | 5.53 |
| Clouding Agent | 2.28 |
| Sodium Carboxymethyl Cellulose (low viscosity) | 0.90 |
| Tricalcium Phosphate | 0.60 |
| Trisodium Citrate (Sodium Citrate) | 0.70 |
| Vitamin C | 0.47 |
| Tenfold Orange Oil | 0.26 |
| Vitamin A | 0.04 |
| Color (Mixture of F.D. & C. No. 5 and F.D. & C. No. 6 Yellow) | 0.01 |
| L-aspartyl-L-Alanine | 1.0 |

Sixty-six grams of the above beverage mix is reconstituted in a pint of water to provide a pleasing beverage.

EXAMPLE X

A beverage mix similar to that of Example IX is prepared by increasing the level of tricalcium phosphate to 1.25 parts and the level of L-aspartyl-L-alanine to 2.0 parts.

EXAMPLE XI

A further beverage mix is prepared from the following dry ingredients:

| Ingredients | Parts |
|---|---|
| Vitamin A | 0.006 |
| Strawberry Colorant | 0.025 |
| Ascorbic Acid | 0.055 |
| Strawberry Flavorant | 0.27 |
| Citric Acid | 1.8 |

-continued

| Ingredients | Parts |
| --- | --- |
| Sucrose | 94. |
| Monocalcium Phosphate | 1.5 |
| L-tyrosyl-L-glutamic acid | 0.5 |

About 24 grams of a composition of this formulation is dissolved in about 8 ounces of water to provide a single serving of a pleasing beverage.

EXAMPLE XII

A beverage mix similar to that of Example XI is prepared by increasing the level of L-tyrosyl-L-glutamic acid to 2.0 parts.

EXAMPLE XIII

A beverage mix similar to that of Example XII is prepared by substituting L-tyrosyl-L-aspartic acid for the L-tyrosyl-L-glutamic acid.

EXAMPLE XIV

A beverage mix similar to that of Example XII is prepared by substituting L-alanyl-L-aspartic acid for the L-tyrosyl-L-glutamic acid.

EXAMPLE XV

An improved table sugar is obtained by mixing 1.0 parts of aspartame or another dipeptide according to the present invention with about 100 parts of sucrose. If desired, the dipeptide can be sprayed on in an aqueous solution while subjecting the sucrose to tumbling in drying air.

EXAMPLE XVI

A gelatin dessert mix is prepared by blending the following dry ingredients:

| Ingredients | Parts |
| --- | --- |
| Sugar | 80.0 |
| Gelatin | 10.0 |
| Citric Acid | 3.0 |
| Trisodium Citrate | 1.2 |
| Fruit Flavor | 0.6 |
| Fruit Color | 0.2 |
| L-aspartyl-L-phenylalanine | 0.5 |

About 85 grams of this mix are mixed with 1 cup of boiling water and stirred to dissolve. To this is added one cup of cold water. The resulting mixture is stirred and chilled to set.

EXAMPLE XVII

A liquid coffee lightener is prepared from the following ingredients:

| Ingredients | Parts |
| --- | --- |
| Sucrose | 46.6 |
| Hydrogenated Coconut Oil | 25.0 |
| Water | 23.4 |
| Sodium stearoyl-2-lactylate | 5.0 |
| Aspartame | 0.5 |

The coffee lightener is prepared by first blending 233 g of sucrose with 25 g of finely ground sodium stearoyl-2-lactylate in a V-Blender for 10 minutes. This mixture is then added slowly to 117 ml of tap water. The water is stirred gently and held at 120° F. After about 10 minutes of stirring, the sodium stearoyl-2-lactylate is evenly dispersed. This dispersion is then transferred to a Waring Blendor and 125 g of hydrogenated coconut oil at 120° F. is added. Blending at high speed is continued for 10 minutes at which point the emulsion temperature reaches 160° F. Upon cooling to room temperature, it gradually loses air to give a translucent pourable emulsion of low viscosity. Upon dilution with distilled water, the dilute emulsion is opaque and has a pH of 6.7. The undiluted emulsion has a water activity of 0.80. This coffee lightener is used in the same manner as cream.

EXAMPLE XVIII

A dried coffee lightener is prepared by employing the same procedure as that in Example XVII but substituting a combination of 40 parts 42 D.E. hydrolyzed cereal solids 2 parts sodium caseinate and 1 part vegetable gum for the sucrose, and spray drying the emulsion.

EXAMPLE XIX

A dried coffee lightener similar to that of Example XVIII is prepared by employing L-aspartyl-L-phenylalanine in place of the aspartame.

EXAMPLE XX

A whipped topping composition is prepared having the following formulation:

| Ingredients | Parts |
| --- | --- |
| Water | 47 |
| Sucrose | 22 |
| Vegetable Gum | 0.8 |
| Sodium Caseinate | 1.2 |
| Hydrogenated Coconut Oil | 26 |
| Polyoxyethylene (20) sorbitan monostearate | 0.7 |
| Sorbitan Monostearate | 0.3 |
| Color & Flavor | 1.6 |
| L-aspartyl-L-phenylalanine | 0.6 |

The dry ingredients are blended together and dispersed in the water at 60° C. using a mechanical stirrer. The fat is then melted and added along with the other ingredients to the aqueous phase. This mixture is blended and thoroughly emulsified while heating on a steam bath. The emulsion is then homogenized in a two-stage Manton-Gaulin homogenizer having a first stage pressure of 7500 psi and a second stage pressure of 500 psi. The homogenized blend is cooled in ice water and whipped.

EXAMPLE XXI

A whipped topping composition similar to that of Example XX is prepared by replacing the L-aspartyl-L-phenylalanine with 1.0 parts of L-tyrosyl-L-glutamic acid.

EXAMPLE XXII

A dry whipped topping mix is prepared having the following formulation:

| Ingredients | Parts |
| --- | --- |
| Hydrogenated Vegetable Oil | 26 |
| Propylene Glycol | |

| Ingredients | Parts |
|---|---|
| Monostearate | 13 |
| Corn Syrup Solids | 7 |
| Sucrose | 46 |
| Lecithin | 0.7 |
| Acetylated Monoglycerides | 0.7 |
| Color and Flavor | 0.1 |
| L-aspartyl-L-glutamic acid | 0.6 |

The emulsion is prepared as in Example XXI but is spray dried in conventional manner. To whip the dry powder, about 170 grams are blended with about ½ cup cold milk and whipped at high speed with a hand mixer for about 2 minutes.

EXAMPLE XXIII

A gelatin dessert similar to that of Example IV is prepared by doubling the amount of aspartame included and offsetting its extended sweetness with about 0.1 parts of alum.

EXAMPLE XXIV

A two week rat feeding study was conducted with male Caesarean-derived Sprague-Dawley rats approximately 200 grams in body weight using the following protocol.

The animals were fed a standard animal chow diet ad libitum throughout the study. They were housed individually in open mesh stainless steel suspended cages in an air conditioned room with the temperature controlled in the range 75° F.±3° F. Fifteen rats were randomly assigned to each test group after blocking on body weight.

The following low pH test beverages were fed to the various test groups:

(1) low pH grape flavored beverage having the following formulation:

| Dry Ingredients | Grams per 1 quart of Beverage |
|---|---|
| Citric Acid | 1.8 |
| Monocalcium Phosphate | 1.5 |
| Grape Flavor | 0.075 |
| Ascorbic Acid | 0.055 |
| Grape Shade | 0.023 |
| Vitamin A | 0.006 |
| Aspartame | 0.55 |

(2) beverage (1) with 100 grams of sucrose per quart of beverage in place of the aspartame;

(3) beverage (1) without monocalcium phosphate, but containing an additional 0.2 grams per quart of citric acid to balance the taste and tartness due to the removal of the monocalcium phosphate;

(4) beverage (3) with 100 grams of sucrose per quart of beverage in place of the aspartame; and (5) deionized water.

After the two week feeding period the rats were sacrificed by decapitation and then the heads were defleshed by scrubbing with a toothbrush after an autoclaving procedure for 20 minutes at 15 pounds pressure.

The mandibular molars were stained by placing them in a 0.125% alcoholic solution of Alizarin Red S, rinsed with water and dried in a hot air oven at 150° F.

After the staining process was completed the lingual surfaces of the molars were scored for the extent of tooth enamel demineralization using a modification of the scoring scale developed by Restarski, *Science*, vol, 102: 404–405, 1945. Before scoring with the aid of a binocular microscope at 13× the molars were assigned random numbers.

The up-take of stain and the extent of ridging were used to estimate the amount of tooth enamel demineralization for each mandibular molar using the following grading scale with an increase in severity:

0-No demineralization, no detectable lingual stain
1-slight demineralization-slight stain
2-mild demineralization, moderate stain
3-moderate demineralization, slight ridging, strong stain
4-moderate demineralization, moderate ridging, ⅓ of dentin exposed
5-strong demineralization, strong ridging, ⅓ to ⅔ of dentin exposed
6-strong demineralization, very strong ridging, greater than ⅔ of dentin exposed.

The results are summarized in the following table:

| | Tooth Enamel Demineralization | |
|---|---|---|
| Beverage | Score | % Decrease Due to Aspartame |
| 1 | 0.8 | 47 |
| 2 | 1.5 | — |
| 3 | 2.5 | 29 |
| 4 | 3.5 | — |
| 5 | 0.2 | — |

Due to the fact that the aspartame can degrade in aqueous system to diketopiperazine and mixtures of diketopiperazine, aspartic acid and phenylalanine, it is suggested that the breakdown products of aspartame are similarly effective in improving dental health as is the aspartame.

EXAMPLE XXV

A 60 day rat feeding study was conducted with weanling Caesarean derived male wistar caries-susceptible rats using the following protocol:

The test group were fed semi-synthetic diets containing 5% alpha-cellulose, 20% lactalbumin, 3% corn oil, 1% AOAC vitamin mix and 3% of a MIT 200 mineral mix modified to contain 30% dicalcium phosphate. The remaining 68% of the diet consisted of either 68% confectionary 10× sucrose or coated corn flakes. The animals were housed in open mesh stainless steel suspended cages in an air conditioned room with the temperature controlled in the range of 75° F.±3° F. Fifteen rats were randomly assigned to each treatment after blocking on body weight.

After the termination of the study, the heads of the animals were autoclaved at 15 pounds pressure for 15 minutes and then the mandibles were removed and cleaned with a coarse bristle toothbrush. After the mandibles are dried, they are stained with 0.0208% murexide in 70% ethanol. After the mandibles are revised and dried, they are scored for caries using a modification of the Keyes method in *J. Dental Research* 37, 1088–99 (1958). The caries scores are a combination of the occlusal and smooth surface caries severity scores on the mandibular molars using scores of 0, 1, 2 and 3 for designating severity of the lesions.

The following treatments were included in the study:

(1) beverage (1) containing aspartame described in EXAMPLE XXIV as the drinking fluid and the semi-synthetic diets containing 68% confectionary 10× sucrose as the carbohydrate.

(2) beverage (2) containing sucrose described in EXAMPLE XXIV as the drinking fluid and the semi-synthetic diet containing 68% confectionary 10× sucrose as the carbohydrate.

(3) distilled water as the drinking fluid and the semi-synthetic diet containing 68% corn flakes containing 0.3% aspartame.

(4) distilled water as the drinking fluid and the semi-synthetic diet containing 68% corn flakes with a 40% sucrose syrup coating in place of the aspartame.

The results are summarized in the following table.

| Treatment | Caries Severity Scores | |
|---|---|---|
| | Score | % Decrease Due to Aspartame |
| 1 | 7.0 | 39 |
| 2 | 11.4 | — |
| 3 | 1.7 | 48 |
| 4 | 3.3 | — |

EXAMPLE XXVI

A 60 day rat feeding study was conducted with weanling Caesarean derived male caries susceptible rats. The protocol was identical to that described in Example XXV with the exceptions that casein was substituted for lactalbumin as the source of protein and the dicalcium phosphate level in the MIT 200 salt mix was decreased to 27.5%. Distilled water was provided as the drinking fluid. The aspartame in the diet replaced part of the alpha cellulose.

The following dietary treatments were included in the study.

(1) Basal cariogenic diet containing 68% confectionary 10× sucrose.

(2) Same as treatment (1) with 0.341% aspartame.

The results summarized in the following table:

| Treatment | Caries Severity Scores | |
|---|---|---|
| | Score | % Decrease Due to Aspartame |
| 1 | 15.5 | — |
| 2 | 11.6 | 25 |

The above disclosure has provided a description of the invention for the purpose of enabling the person skilled in the art how to make and use the same and has not been made for the purpose of detailing all things known or obvious to the skilled worker. Upon reading this disclosure, many modifications and variations of this invention will become apparent to those skilled in the art. It is intended that all such modifications and variations be included within the scope of the present invention which is defined by the following claims.

What is claimed is:

1. A method of reducing the demineralization of tooth enamel caused by contacting said enamel with an acid-containing food product which normally fosters tooth enamel demineralization comprising the step of adding to said food product, aspartame in an amount that produces excess sweetness and a sweetness modulating material.

2. A method according to claim 1 wherein the food product is a beverage having a pH below 6.0, each quart of beverage containing from 0.015 to 0.15 gram equivalents of an edible food acid selected from the group of acids consisting of citric, malic, adipic, fumaric, ascorbic and combinations thereof.

3. A method according to claim 2 wherein sucrose is employed at a level from about 25 to 100 grams per quart of beverage.

4. The method according to claim 2 wherein the amount of aspartame is from about 0.25 to about 2.0 grams per quart of beverage or an amount of dry mix for preparing said beverage.

5. The method according to claim 1 wherein aspartame is used in combination with sweeteners selected from the group consisting of natural sweeteners, synthetic sweeteners and combinations thereof the level of sweetness is reduced by adding a sweetness modulating material selected from the group consisting of alum and naringin.

6. The method according to claim 5 wherein the natural sweetener is sucrose.

7. The method according to claim 6 wherein from about 0.1 to about 10.0 parts of aspartame is used for each 100 parts of sucrose.

* * * * *